Sept. 10, 1940. J. D. BROWNELL Plant Pat. 420
ROSE
Filed Feb. 9, 1940
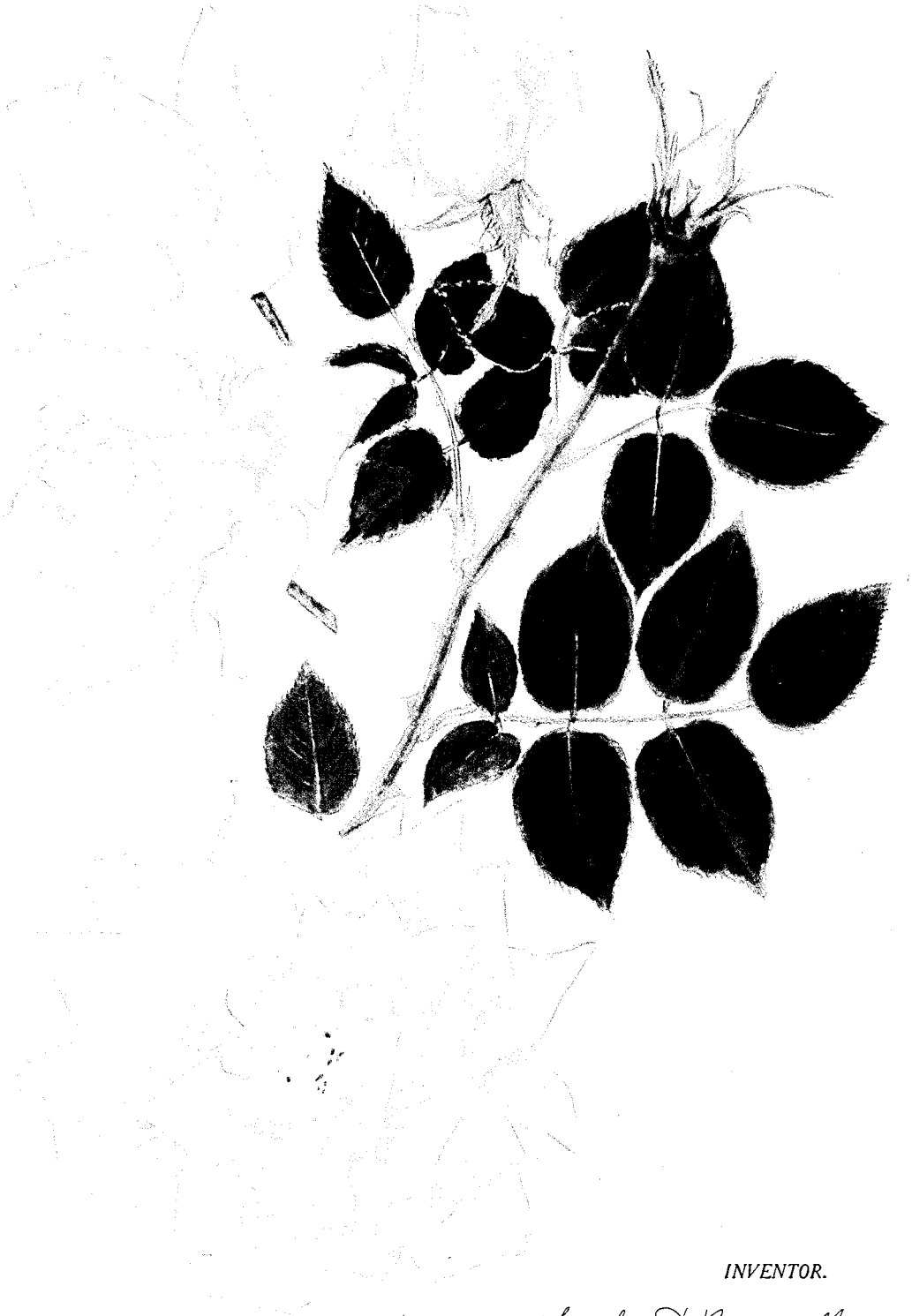
INVENTOR.
Josephine D. Brownell.

Patented Sept. 10, 1940

Plant Pat. 420

UNITED STATES PATENT OFFICE

420

ROSE

Josephine D. Brownell, Little Compton, R. I.

Application February 9, 1940, Serial No. 318,073

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by propagation, selection, and cross pollenation, which can be and has been asexually reproduced.

My new rose is new as to the following characteristics and especially as to their joint association with the characteristics inherited from *Rosa wichuraiana,* of hardiness or immunity from serious injury on account of cold temperatures prevailing in certain parts of the northern United States;

The unique, nearly white to nearly pure yellow shades, (ordinary dictionary definition) of its petals, the unusual brilliance and luster thereof and their tendency to hold these colors under exposure;

The novelty and variation within certain definite limits of the form of the bloom, its character of holding that form for a long time and the large size of the flowers;

Its character of fragrance;

Its remontant and everblooming or reblooming habit,

Its unusual abundance of flowers, notably after early bloom time until frost,

Its character of ascending in height by recurrent branching.

In the accompanying drawing forming a part of this specification I have shown my new rose in its natural colors, that is, as near as is possible to do so artificially. As the plant develops in growth many of the leaflets mature in size to about twice the relative size as shown in the drawing. A seven leafleted leaf is also shown as this frequently occurs on my new rose plant and frequently on flower stems of descendents of *Rosa wichuraiana,* but seldom on commercial forms of hybrid teas.

My new rose plant is otherwise described as follows.

Essential Information

*Type*

Hybrid tea, *Rosa wichuraiana* hybrid, dwarf to ascending to tall for garden display, cut flower and pot forcing.

*Class*

Hybrid tea crossed with *Rosa wichuraiana.*

*Breeding or discovery*

This rose plant was bred by me and under my directions by propagation and cross pollenation. It is a seedling grown from a seed produced on the hardy climbing *Rosa wichuraiana* hybrid known as "Glendale," this seed was produced by fertilization with pollen of a self seedling from the hardy climbing *Rosa wichuraiana* hybrid known as "Golden Climber, Mrs Arthur Curtiss James".

This pollenation was directed by me and performed by emasculating a flower and placing thereon a bag protecting from foreign and self pollen. This bag was later removed and the flower was hand pollenated with a camel's hair brush and the bag immediately replaced.

The date of this pollen cross was June 30, 1933.*

The seed was planted December 15, 1933, and the date of the first flower was July 10, 1934.

The plant and flower seemed to me to be of unusual merit and I have since made and directed extensive propagations and tests thereof in the United States and in foreign countries of the variety.

Plants of this variety budded from this seedling on *Rosa multiflora* root stock, have after being entirely exposed to moderate subzero temperatures, survived and bloomed normally the following season in the hybrid tea manner. The variety has been propagated by budding at Little Compton, Rhode Island, in the months of July and August in 1934–38 inclusive and the characters have successively reproduced, true to the original seedling.

Flower

*Habit*

It blooms outdoors in Little Compton, Rhode Island, beginning about three days prior to the average beginning time of commercial hybrid teas and continuous relatively to the growth of the plant until frost.

* This and other dates herein are approximate.

*Flowers borne*

Often one, frequently two or three and sometimes more on each stem in the hybrid tea type of cluster; pedicels and peduncles are medium in length and diameter, erect, stiff, almost smooth, free from large prickles and bristles but with a few tiny prickles to small hairs. Stems are long, notably strong, diameter medium to slightly large and notably rigid.

*Quantity of bloom*

Free to abundant, being cumulative in quantity of florescence from year to year as the plant increases in size, notably free flowering in midsummer, being of much greater bloom quantity and continuity when well grown than most hybrid teas in commerce.

*Fragrance*

Mild to delicate, pleasing China Tea in combination with *Rosa wichuraiana* under favorable conditions.

*Bud*

Neck normal as described, opens well, being little to not at all affected by hot or wet weather or both, as to color and form, except at very high temperatures the color is less intense and the form of the petals is less recurled.

Before the calyx breaks the size is medium, form pointed, frequently with one or more sepals with foliaceous parts extending beyond the apex in some buds as much as one-half inch, the number and size of the foliaceous appendages being variable and frequently having one narrow, pointed serrate appendage on each side of the sepals, otherwise the sepals are usually normal and regular, tapering to nearly lanceolate near the apex. Under vigorous growth an occasional bud has a sixth sepal which usually overlaps in part one of the normal sepals.

Color of the bud as the calyx opens, varies somewhat dependent upon environment. As the normal greenish (ordinary dictionary definition) color of the unmature petals disappears the color of the outer petals is a combination of White and Lemon Yellow.*

This color combination extends throughout all of the petals. Usually each row of petals toward the center is more Lemon Yellow and less White than the next outer row of petals. There is usually no appreciable difference in color of one side of any petal from the other. Under favorable conditions the innermost row of petals is usually substantially all Lemon Yellow.

*Bloom*

The flower is usually 4 to 5½ inches in diameter when fully open, infrequently more or less; very double having petals variable in number usually from thirty to forty with some narrow petals and petaloids in the center variable in number. The flower opens slowly, high centered, recurled, usually showing stamens at maturity. The petals are variable from obovate to ovate with inner petals of narrow irregular variable forms, outer and intermediate petals recurl outward, frequently notched once at the outer apex. Texture is medium to thick and leathery, both sides satiny to shiny.

Color of opening flower and of the open flower is as described under bud. The petals are substantial and after about five days drop off cleanly. The flower does not "ball" in wet weather at Little Compton, Rhode Island. The flower lasts well, is not affected at any stage by moderate cold or hot temperatures or humidity or wet weather. This new variety may be grown to bloom two to three times as many flowers per season as the average hybrid tea in commerce, also to bloom more constantly through midseason.

*Reproductive organs*

Stamens, quantity medium, of slightly uneven, medium length.

Anthers, Light Salmon Orange.

Filaments, nearly Mustard Yellow.

Pistils are several, of slightly uneven length, about ½ inch long.

Styles are Chalcedony Yellow.

Stigmas are Citron Yellow, the pollen is moderate in quantity.

Ovaries are usually all enclosed.

Hips rarely develop at Little Compton, Rhode Island, form globular, color nearly like under side of leaves with variable overlay on the side exposed to the sun, smooth, walls moderately thin, fleshy.

Sepals are persistent.

Seeds variable, no germination yet noted.

PLANT

*Foliage*

Is abundant to normal of compound leaves usually of three or five leaflets near the flower, five and frequently seven leafleted leaves lower down on the stem. Size of leaflets variable from medium small to medium hybrid tea size. The accompanying picture shows relatively the smaller sizes of leaflets. Form of leaflets usually ovate with apex moderately acute, somewhat variable to wider and narrower, base rounded on short petiolules; margins slightly irregularly serrated by medium sized and pointed serrations. Color of the leaflets grown at Little Compton, Rhode Island, is upper side Medium Dark Green to Forest Green, under side Bice Green with a variable shading of Dahlia Carmine on the serrate edges and along the ribs.

The rachises are medium with minute hairs on the edges and variable unmature prickles on the under side, colors relatively comparable with that of leaves.

The stipules are medium long, varying around ¾ inch in length and medium width, with normal points that spread in relation to each other slightly more than 90 degrees. The edges are minutely hairy.

Stems are medium to large and when well grown and established after several years are often notably large, and grow much larger as branches extend from them. The bark is nearly Bice Green, variable, overload slightly with Dahlia Carmine. The prickles are nearly Dahlia Carmine and slightly variable in color turning to lighter and losing their color. Form of prickles is sharp pointed and nearly straight. Size averages about ⅜ inch.

Disease, notably free from defoliation on account of mildew and blackspot.

*Growth*

Habit, dwarf becoming bushy. The growth is moderately free at first, developing each year thereafter under favorable vegetative opportunity into a larger bush by cumulative growth in much the same manner as do shrubbery species that

* Color references unless otherwise specified are to Ridgway.

survive in nature and in distinction from the manner of growth of most hybrid tea varieties.

*Winter resistance*

One of the notable characters of my new rose is its resistance to moderate subzero temperatures in combination with its hybrid tea type and its *Rosa wichuraiana* ancestry. This variety budded with bud entirely exposed above ground to temperatures as low as 12 degrees below zero Fahrenheit at Little Compton, Rhode Island, survived and bloomed normally the following season. This plant so exposed to such subzero temperatures is affected thereby to the extent of at least a part of the stems and branches being injured and killed back. The growth of this plant in the garden exposed to temperatures below ten below zero may be compared with the growth of garden forms of herbaceous peonies. This plant planted in the bed normally with budded eye about three inches below bed level, may under certain subzero exposure kill back to the ground, and normal growth from new eyes below ground will usually develop the plant by bloom time into a normal hybrid tea rose bush. This plant exposed to temperatures only above ten below zero usually will if well grown, retain all or a substantial part of the branches and stems in living condition and proceed to extend growth upwards as described.

*Longevity*

As a natural consequence of the foregoing described characters the expected longevity of this plant is substantially greater than that of forms of hybrid teas in commerce and from tests and data obtained has the probable expectancy of several times ten times that of the average hybrid tea rose in commerce. The new and distinct characteristics of my new rose plant variety as herein described are typical of many such varieties being produced by me. These are in fact *Rosa wichuraiana* hybrid tea hybrids.

*Comparisons*

The flower is more nearly like the flower of the hardy climbing rose variety "Elegance" than any other rose known to me. In comparison with other hybrid tea roses known to me, it is differentiated by being a more vigorous plant that can produce when established more than twice as many flowers, has frequently seven leaflets, a distinctive resistance to winter exposure and cumulative growth from year to year, with winter survival, greater expectancy of longevity and sustained rebranching. The flower in comparison with other yellow hybrid teas is more brilliant and lustrous. As compared with the variety "Mrs Earshine Pembroke Thom" which it somewhat resembles, the yellow color is more pure and has less red in its color combination, the petals are more shiny and more recurled and the plant can produce more than twice as many flowers per season.

I claim:

The rose variety substantially as shown and described characterized by its new and distinctive constitution including resistance to winter injury, its continuity and intensity of florescence, its pleasing fragrance, its long keeping character, the form of its petals, its character of long holding its flower form, its unique color combinations of yellow and white, all in association with its habit of branching and cumulative growth.

JOSEPHINE D. BROWNELL.